US00PP21615P2

(12) United States Plant Patent
Wood

(10) Patent No.: US PP21,615 P2
(45) Date of Patent: Jan. 11, 2011

(54) ***SPIRAEA* PLANT NAMED 'YAN'**

(50) Latin Name: *Spiraea japonica*
Varietal Denomination: Yan

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/462,571

(22) Filed: Aug. 5, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—June Hwu
(74) *Attorney, Agent, or Firm*—C. A. Whealy

(57) ABSTRACT

A new and distinct cultivar of *Spiraea* plant named 'Yan', characterized by its compact, upright, outwardly spreading and mounding plant habit; vigorous growth habit; freely branching habit; leaves that are yellow green in color; numerous pink-colored flowers; good garden performance; and resistance to Powdery Mildew.

2 Drawing Sheets

Botanical designation: *Spiraea japonica.*
Cultivar denomination: 'YAN'.

CROSS-REFERENCED TO RELATED APPLICATIONS

Applicant: Timothy D. Wood
Title: *Spiraea* Plant Named 'Galen'
Filed: U.S. Plant patent application Ser. No. 12/583,682.

BACKGROUND OF THE INVENTION

The present invention relates to a new and distinct cultivar of *Spiraea* plant, botanically known as *Spiraea japonica* and hereinafter referred to by the name 'Yan'.

The new *Spiraea* plant is a product of a planned breeding program conducted by the Inventor in Grand Haven, Mich. The objective of the breeding program is to develop new compact *Spiraea* cultivars with strong foliage, large flowers and resistance to Powdery Mildew.

The new *Spiraea* plant originated from an open-pollination during the summer of 2004 of *Spiraea japonica* 'Walbuma', disclosed in U.S. Plant Pat. No. 9,363, as the female, or seed, parent with an unknown selection of *Spiraea japonica,* as the male, or pollen, parent. The new *Spiraea* plant was discovered and selected by the Inventor during the summer of 2006 as a single flowering plant within the progeny of the stated open-pollination in a controlled environment in Grand Haven, Mich.

Asexual reproduction of the new *Spiraea* plant by softwood cuttings in a controlled greenhouse environment in Grand Haven, Mich. since the summer of 2006 has shown that the unique features of this new *Spiraea* plant are stable and reproduced true to type in successive generations of asexual reproduction.

SUMMARY OF THE INVENTION

Plants of the new *Spiraea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Yan'. These characteristics in combination distinguish 'Yan' as a new and distinct cultivar of *Spiraea:*

1. Compact, upright, outwardly spreading and mounding plant habit.
2. Vigorous growth habit.
3. Freely branching habit.
4. Leaves that are yellow green in color.
5. Numerous pink-colored flowers.
6. Good garden performance.
7. Resistance to Powdery Mildew.

Plants of the new *Spiraea* can be compared to plants of the female parent, 'Walbuma'. Plants of the new *Spiraea* differ from plants of 'Walbuma' in the following characteristics:

1. Plants of the new *Spiraea* are more compact than plants of 'Walbuma'.
2. Plants of the new *Spiraea* are more freely branching than plants of 'Walbuma'.
3. Plants of the new *Spiraea* have larger leaves than plants of 'Walbuma'.
4. Plants of the new *Spiraea* and 'Walbuma' differ in leaf color as plants of 'Walbuma' have golden-colored leaves.
5. Plants of the new *Spiraea* and 'Walbuma' differ slightly in flower color.
6. Plants of the new *Spiraea* are more resistant to Powdery Mildew than plants of 'Walbuma'.

Plants of the new *Spiraea* can be compared to plants of the *Spiraea japonica* 'Galen', disclosed in a U.S. Plant patent application filed concurrently with this application. Plants of the new *Spiraea* differ from plants of 'Galen' in the following characteristics:

1. Plants of the new *Spiraea* are more compact than plants of 'Galen'.
2. Plants of the new *Spiraea* and 'Galen' differ in leaf color.
3. Plants of the new *Spiraea* are not as freely flowering as plants of 'Galen'.

4. Plants of the new *Spiraea* and 'Galen' differ in flower color as plants of 'Galen' have purple-colored flowers.

Plants of the new *Spiraea* can also be compared to plants of the *Spiraea japonica* 'Gold Mound', not patented. In side-by-side comparisons conducted in Grand Haven, Mich., plants of the new *Spiraea* differed from plants of 'Gold Mound' in the following characteristics:

1. Plants of the new *Spiraea* were shorter than plants of 'Gold Mound'.
2. Plants of the new *Spiraea* and 'Gold Mound' differed in flower color.
3. Plants of the new *Spiraea* were more resistant to Powdery Mildew than plants of 'Gold Mound'.

BRIEF DESCRIPTION OF THE PHOTOGRAPHS

The accompanying colored photographs illustrate the overall appearance of the new *Spiraea* plant, showing the colors as true as it is reasonably possible to obtain in colored reproductions of this type. Colors in the photographs may differ slightly from the color values cited in the detailed botanical description which accurately describe the colors of the new *Spiraea* plant.

The photograph on the first sheet is a side perspective view of a typical plant of 'Yan' grown in an outdoor nursery.

The photograph on the second sheet is a close-up view of typical inflorescences and leaves of 'Yan'.

DETAILED BOTANICAL DESCRIPTION

The aforementioned photographs and following observations, measurements and values describe plants of the new *Spiraea* grown in three-gallon containers in Grand Haven, Mich. during the spring and early summer in a polyethylene-covered greenhouse and under conditions which closely approximate commercial production. Plants were three years old when the photographs and the description were taken. In the description, color references are made to The Royal Horticultural Society Colour Chart, 1995 Edition, except where general terms of ordinary dictionary significance are used.

Botanical classification: *Spiraea japonica* 'Yan'.

Parentage:

*Female, or seed, parent.*—*Spiraea japonica* 'Walbuma', disclosed in U.S. Plant Pat. No. 9,363.

*Male, or pollen, parent.*—Unknown selection of *Spiraea japonica,* not patented.

Propagation:

*Type.*—By softwood cuttings.

*Time to initiate roots.*—About 15 days at 22° C.

*Time to produce a rooted young plant.*—About two months at 22° C.

*Root description.*—Fine to thick, fibrous; cream to brown in color.

*Rooting habit.*—Freely branching; dense.

Plant description:

*Plant form and growth habit.*—Perennial shrub; compact, upright, outwardly spreading and mounding plant habit; vigorous growth habit.

*Branching habit.*—Freely branching habit with about 15 primary lateral branches; pinching (removal of terminal apices) will enhance lateral branch development.

*Plant height.*—About 44 cm.

*Plant diameter* (*area of spread*).—About 55 cm.

Lateral branch description:

*Length.*—About 8 cm.

*Diameter.*—About 1 mm.

*Internode length.*—About 1 cm.

*Texture.*—Slightly pubescent.

*Color.*—Close to 144B.

Foliage description:

*Arrangement.*—Alternate or whorled, simple.

*Length.*—About 4 cm.

*Width.*—About 3 cm.

*Shape.*—Ovate to lanceolate.

*Apex.*—Acute.

*Base.*—Cuneate.

*Margin.*—Serrate to doubly serrate.

*Texture, upper and lower surfaces.*—Smooth, glabrous.

*Venation pattern.*—Pinnate.

*Color.*—Developing leaves, upper surface: Close to 144C. Developing leaves, lower surface: Close to 144A. Fully expanded leaves, upper surface: Close to 149A; venation, similar to surface color. Fully expanded leaves, lower surface: Close to 147C; venation, similar to surface color.

*Petiole.*—Length: About 3 mm. Diameter: About 1 mm. Texture, upper and lower surfaces: Smooth, glabrous. Color, upper and lower surfaces: Close to 144B.

Flower description:

*Flower appearance/arrangement.*—Single rotate flowers arranged in compound corymbs; freely flowering habit with usually about 73 flowers per inflorescence; flowers face upright to outwardly.

*Natural flowering season.*—Continuous flowering from the late spring through the summer in Grand Haven, Mich.

*Fragrance.*—Faintly fragrant; sweet, pleasant.

*Inflorescence height.*—About 2 cm.

*Inflorescence diameter.*—About 3 cm.

*Flower diameter.*—About 5 mm.

*Flower length* (*height*).—About 6 mm.

*Flower bud.*—Length: About 2 mm. Diameter: About 2 mm. Shape: Globose. Color: Close to 63A.

*Petals.*—Quantity per flower: Single whorl of five. Length: About 2 mm. Width: About 2 mm. Shape: Ovate to elliptical. Apex: Obtuse to acute. Margin: Entire. Texture, upper and lower surfaces: Smooth, glabrous. Color: When opening, upper surface: Close to 63A. When opening, lower surface: Close to 63B. Fully opened, upper surface: Close to 63C. Fully opened, lower surface: Close to 64D.

*Sepals.*—Quantity per flower: Single whorl of five. Length: About 2 mm. Width: About 2 mm. Shape: Rounded. Apex: Acute. Base: Truncate. Margin: Entire. Texture, upper and lower surfaces: Smooth, glabrous. Color: When opening, upper surface: Close to 165B. When opening, lower surface: Close to 144B. Fully opened, upper surface: Close to 176C. Fully opened, lower surface: Close to 145B.

*Peduncles.*—Length: About 2 cm. Diameter: About 1 mm. Strength: Strong. Texture: Smooth, glabrous. Color: Close to 145A.

*Pedicels.*—Length: About 3 mm. Diameter: About 0.5 mm. Strength: Strong. Texture: Smooth, glabrous. Color: Close to 145A.

*Reproductive organs.*—Androecium: Quantity per flower: About eleven. Anther shape: Globose. Anther length: About 0.5 mm. Anther color: Close to 61A. Amount of pollen: Scarce. Pollen color: Close to 4D. Gynoecium: Quantity per flower: One. Pistil length: About 1.5 mm. Style length: About 1 mm. Style color:

Close to 60B. Stigma appearance: Globose. Stigma color: Close to 60B. Ovary color: Close to 145B.

*Seeds.*—Length: About 1 mm. Diameter: About 0.5 mm. Color: Close to 151A.

Garden performance: Plants of the new *Spiraea* have been observed to have good garden performance and to tolerate rain, wind and temperatures ranging from about −31° C. to about 38° C.

Pathogen/pest resistance: Plants of the new *Spiraea* have been observed to be resistant to Powdery Mildew. Plants of the new *Spiraea* have not been observed to be resistant to pests and other pathogens common to *Spiraea*.

It is claimed:

1. A new and distinct *Spiraea* plant named 'Yan' as illustrated and described.

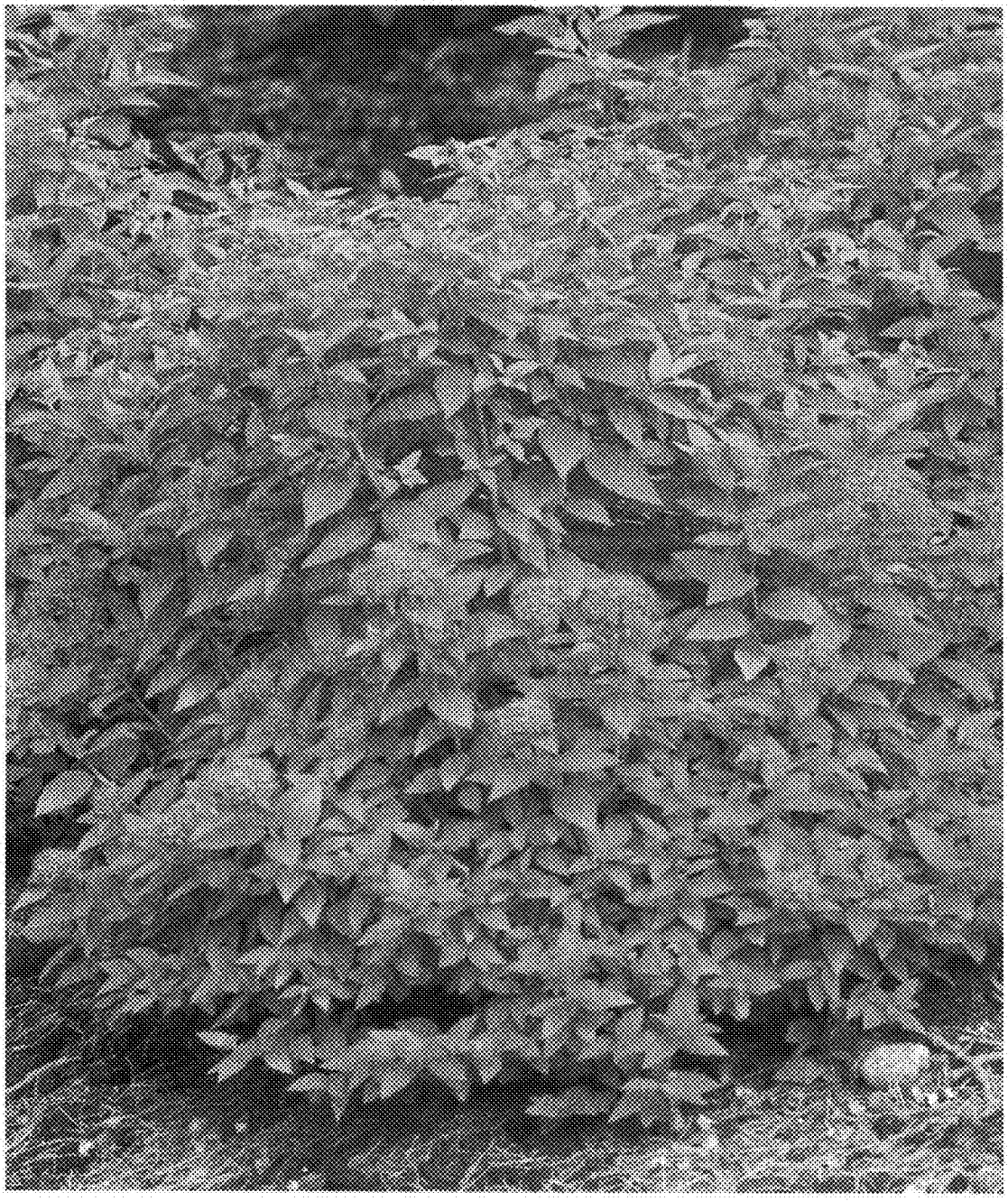

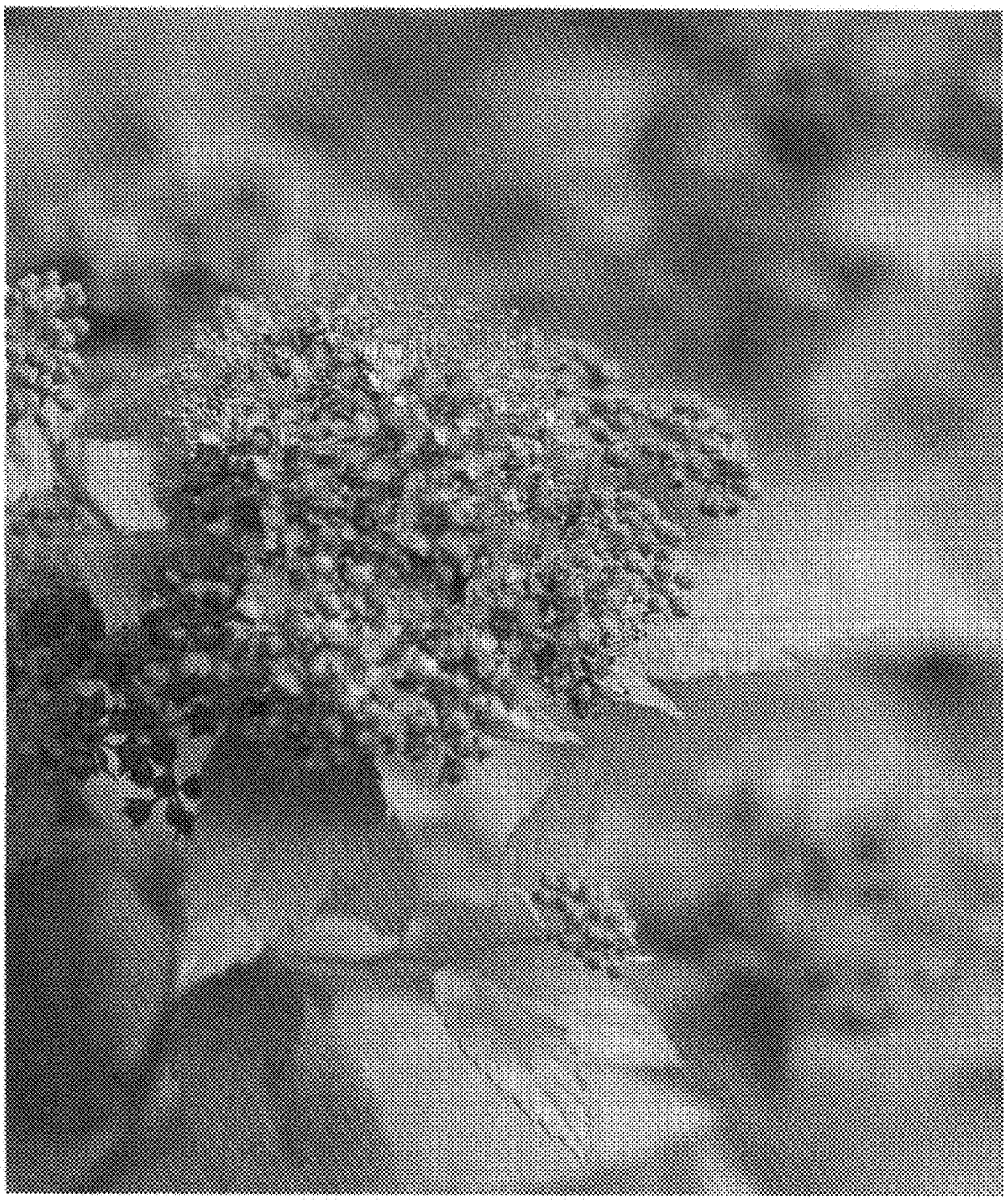

* * * * *